US012629161B2

(12) United States Patent
Goyal

(10) Patent No.: US 12,629,161 B2
(45) Date of Patent: May 19, 2026

(54) CATHETER SYSTEMS FOR ACCESSING THE BRAIN FOR TREATMENT OF ISCHEMIC STROKE

(71) Applicant: MG Stroke Analytics Inc., Calgary (CA)

(72) Inventor: Mayank Goyal, Calgary (CA)

(73) Assignee: MG Stroke Analytics Inc., Calgary (CA)

( * ) Notice: Subject to any disclaimer, the term of this patent is extended or adjusted under 35 U.S.C. 154(b) by 0 days.

(21) Appl. No.: 18/403,108

(22) Filed: Jan. 3, 2024

(65) Prior Publication Data

US 2024/0130744 A1      Apr. 25, 2024

Related U.S. Application Data

(63) Continuation of application No. 16/070,926, filed as application No. PCT/CA2018/050151 on Feb. 9, 2018, now Pat. No. 11,896,245.

(60) Provisional application No. 62/457,082, filed on Feb. 9, 2017.

(51) Int. Cl.
| | |
|---|---|
| *A61B 17/22* | (2006.01) |
| *A61B 17/00* | (2006.01) |
| *A61M 25/00* | (2006.01) |
| *A61M 25/10* | (2013.01) |

(52) U.S. Cl.
CPC ......... *A61B 17/22* (2013.01); *A61M 25/0068* (2013.01); *A61M 25/10* (2013.01); *A61B 2017/00292* (2013.01); *A61B 2017/22038* (2013.01); *A61B 2017/22051* (2013.01);
(Continued)

(58) Field of Classification Search
None
See application file for complete search history.

(56) References Cited

U.S. PATENT DOCUMENTS

| | | |
|---|---|---|
| 5,102,415 A | 4/1992 | Guenther et al. |
| 5,120,323 A | 6/1992 | Shockey et al. |
| 6,080,140 A | 6/2000 | Swaminathan et al. |
| (Continued) | | |

FOREIGN PATENT DOCUMENTS

| | | |
|---|---|---|
| WO | WO2011/032038 A1 | 3/2011 |
| WO | WO2017/139894 A1 | 8/2017 |
| WO | WO2018/145212 A1 | 8/2018 |

OTHER PUBLICATIONS

European Patent Office, Extended European Search Report dated Jul. 13, 2022 in European Patent Application No. 20843137.9, 8 pages.
(Continued)

*Primary Examiner* — Elizabeth Houston
*Assistant Examiner* — Lindsey Bachman
(74) *Attorney, Agent, or Firm* — Inskeep IP Group, Inc.

(57) ABSTRACT

The invention describes catheter systems and methods for accessing the brain during endovascular/neurointervention procedures in the treatment of ischemic stroke. More specifically, a multi-axial catheter system and kit is described that improves the process of accessing a carotid artery particularly in patients having a tortuous aortic arch and thereafter improves the process of gaining access to the brain to enable the insertion of aspiration and/or the deployment clot retrieval devices. In addition, methods of utilizing these systems are described.

19 Claims, 13 Drawing Sheets

(52) U.S. Cl.
CPC .............. *A61B 2017/22069* (2013.01); *A61B*
*2017/22079* (2013.01)

(56)                      References Cited

U.S. PATENT DOCUMENTS

| | | | |
|---|---|---|---|
| 7,749,196 | B2 | 7/2010 | Osborne et al. |
| 7,771,369 | B2 | 8/2010 | Griffin et al. |
| 8,118,804 | B2 | 2/2012 | Takagi et al. |
| 8,157,760 | B2 | 4/2012 | Criado et al. |
| RE45,380 | E | 2/2015 | Root et al. |
| RE45,760 | E | 10/2015 | Root et al. |
| RE45,776 | E | 10/2015 | Root et al. |
| RE46,116 | E | 8/2016 | Root et al. |
| 9,980,838 | B2 * | 5/2018 | Syed ........................ A61F 2/954 |
| 10,213,582 | B2 | 2/2019 | Garrison et al. |
| 10,456,555 | B2 | 10/2019 | Garrison et al. |
| 10,646,239 | B2 | 5/2020 | Garrison et al. |
| 11,871,944 | B2 | 1/2024 | Garrison et al. |
| 11,925,770 | B2 | 3/2024 | Chou et al. |
| 2005/0216044 | A1 * | 9/2005 | Hong ..................... A61B 17/22 |
| | | | 604/528 |
| 2005/0273074 | A1 | 12/2005 | Lewis |
| 2006/0264905 | A1 | 11/2006 | Eskridge et al. |

| | | | |
|---|---|---|---|
| 2009/0076447 | A1 | 3/2009 | Casas et al. |
| 2011/0202038 | A1 * | 8/2011 | Gill ................. A61M 25/09041 |
| | | | 604/528 |
| 2012/0065660 | A1 * | 3/2012 | Ferrera ................ A61B 17/221 |
| | | | 606/198 |
| 2012/0172798 | A1 | 7/2012 | Miller et al. |
| 2012/0197284 | A1 | 8/2012 | Ogle et al. |
| 2014/0358123 | A1 | 12/2014 | Ueda et al. |
| 2015/0105809 | A1 * | 4/2015 | Connolly .......... A61M 25/0147 |
| | | | 606/159 |
| 2015/0174368 | A1 | 6/2015 | Garrison et al. |
| 2016/0220741 | A1 * | 8/2016 | Garrison .......... A61M 25/0054 |
| 2017/0030409 | A1 | 2/2017 | Wada |
| 2017/0239447 | A1 * | 8/2017 | Yang .................... A61M 25/10 |
| 2018/0085167 | A1 | 3/2018 | Goyal |
| 2018/0250498 | A1 | 9/2018 | Stern et al. |
| 2020/0406018 | A1 * | 12/2020 | Malek ............... A61M 39/0247 |
| 2024/0139471 | A1 * | 5/2024 | Kessler ............. A61M 25/0054 |

OTHER PUBLICATIONS

WIPO, Canadian International Search Authority, International Search
Report and Written Opinion mailed Apr. 24, 2018 in International
Patent Application No. PCT/CA2018/050151, 12 pages.

* cited by examiner

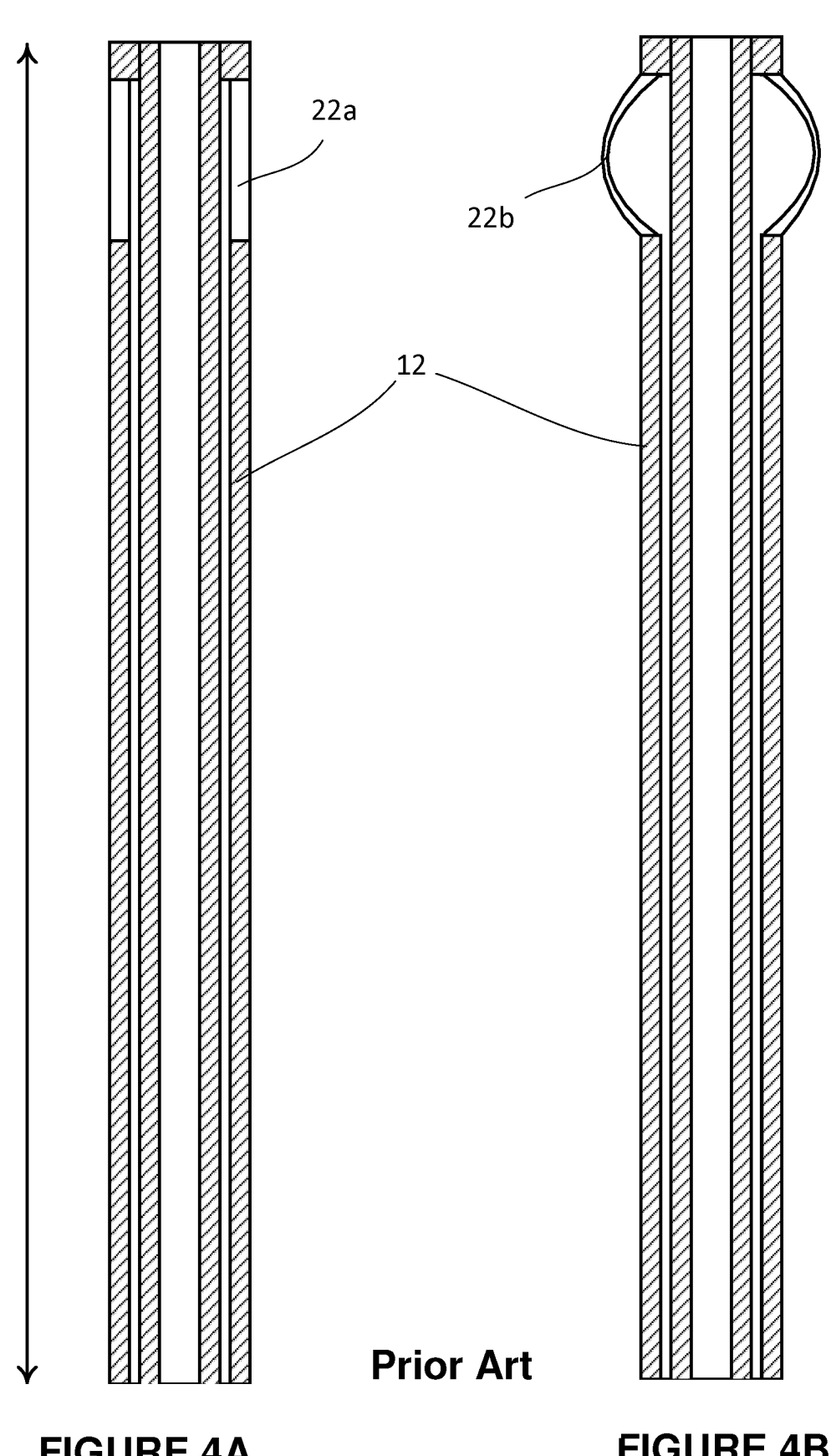
22a
22b
12
Prior Art
FIGURE 4A          FIGURE 4B

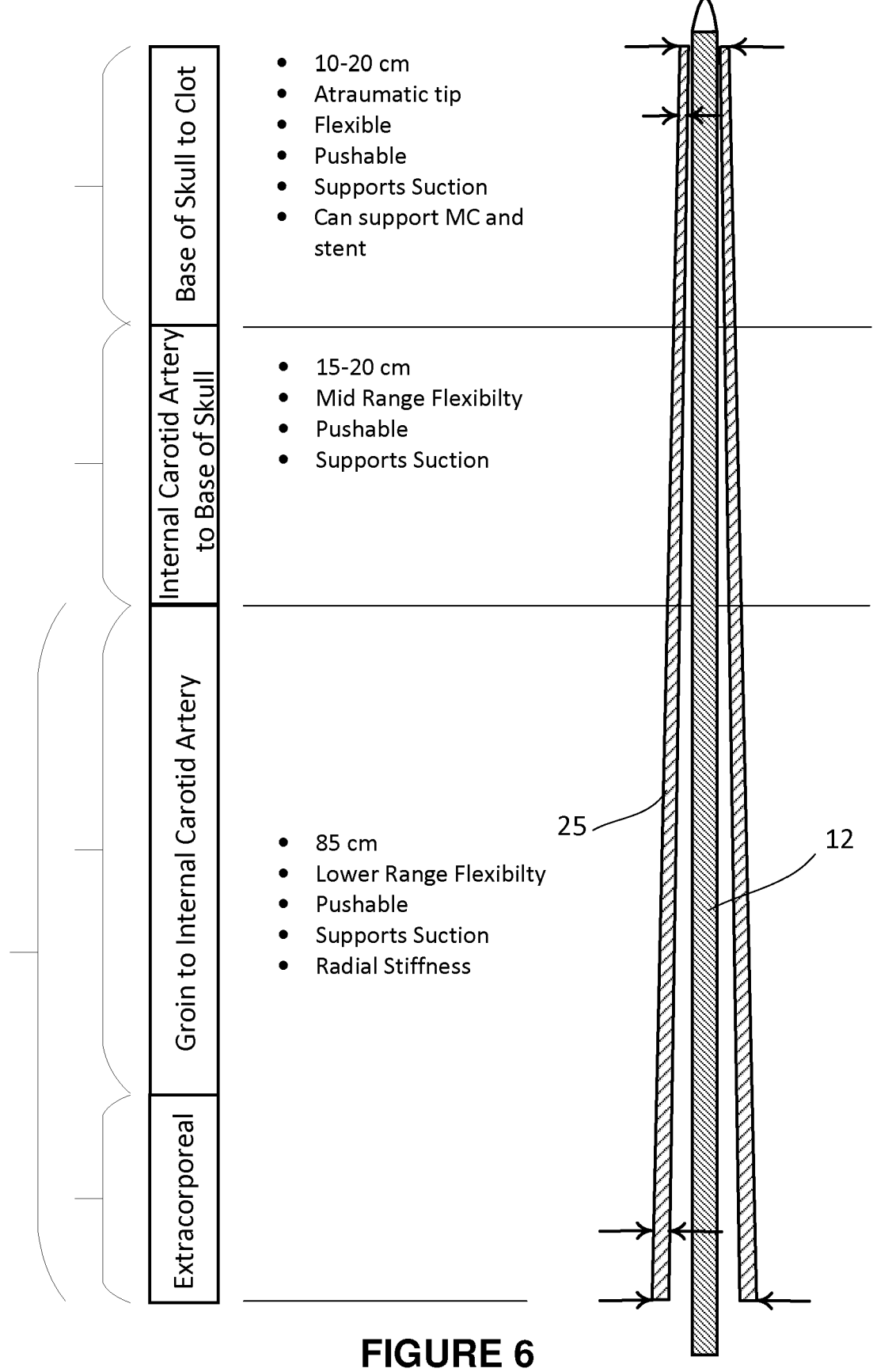

| Base of Skull to Clot | • 10-20 cm<br>• Atraumatic tip<br>• Flexible<br>• Pushable<br>• Supports Suction<br>• Can support MC and stent |
| Internal Carotid Artery to Base of Skull | • 15-20 cm<br>• Mid Range Flexibilty<br>• Pushable<br>• Supports Suction |
| Groin to Internal Carotid Artery | • 85 cm<br>• Lower Range Flexibilty<br>• Pushable<br>• Supports Suction<br>• Radial Stiffness |
| Extracorporeal | |

Base of Skull to Clot

- 10-20 cm
- Atraumatic tip
- Flexible
- Pushable
- Supports Suction
- Can support MC and stent Internal Carotid Artery to Base of Skull

- 15-20 cm
- Mid Range Flexibilty
- Pushable
- Supports Suction

Groin to Internal Carotid Artery

- 85 cm
- Lower Range Flexibilty
- Pushable
- Supports Suction
- Radial Stiffness Extracorporeal

26

25

12

14

Base of Skull to Clot

Common Carotid Artery to Base of Skull

Groin to Internal Carotid Artery

GW

DC

G2B

GC

Base of Skull to Clot

Common Carotid Artery to Base of Skull

Groin to Internal Carotid Artery

GW

DC

G2B

GC

Base of Skull to Clot

Common Carotid Artery to Base of Skull

Groin to Internal Carotid Artery

GW

G2B

DC

GC

CATHETER SYSTEMS FOR ACCESSING THE BRAIN FOR TREATMENT OF ISCHEMIC STROKE

RELATED APPLICATIONS

This application is a continuation of U.S. patent application Ser. No. 16/070,926 entitled Catheter Systems For Accessing The Brain For Treatment Of Ischemic Stroke, which is a U.S. National Phase application under 35 U.S.C. § 371 of and claims priority to International Patent Application No. PCT/CA2018/050151, International Filing Date Feb. 9, 2018, entitled Catheter Systems For Accessing The Brain For Treatment Of Ischemic Stroke, which claims benefit of and priority to U.S. Provisional Application Ser. No. 62/457,082 filed Feb. 9, 2017 entitled Catheter Systems For Accessing The Brain For Treatment Of Ischemic Stroke all of which are hereby incorporated herein by reference in their entireties.

FIELD OF THE INVENTION

The invention describes catheter systems and methods for accessing the brain during endovascular/neurointervention procedures in the treatment of ischemic stroke. More specifically, a multi-axial catheter system and kit is described that improves the process of accessing a carotid artery particularly in patients having a tortuous aortic arch and thereafter improves the process of gaining access to the brain to enable the insertion of aspiration and/or the deployment clot retrieval devices. In addition, methods of utilizing these systems are described.

BACKGROUND OF THE INVENTION

The human body is an extensive network of blood vessels including the venous and arterial systems for circulating blood throughout the body. The occurrence and/or development of restrictions to flow within the circulatory system can result in serious medical conditions, the most significant being myocardial infarction and ischemic stroke. The treatment of both conditions (and others involving the circulatory system) continues to evolve with many new techniques and equipment being utilized to effect treatment.

In recent years, a variety of traumatic surgical procedures have been replaced with procedures that involve the use of one or more catheters being advanced through the vascular system of the body to gain access to diagnose and/or treat issues involving the vasculature of a particular organ. For example, ischemic strokes caused by blood clot blockages in the brain, coronary artery blockages within the heart and various heart defects may be treated by advancing catheter systems to the affected site whence various procedures can be initiated to treat the problem. In both the treatment of both coronary artery circulation issues and ischemic strokes, various stents having various structural and functional properties can be positioned and deployed at a location where intervention is required.

Catheter procedures are also undertaken in other parts of the body including the leg vessels and renal arteries and other complex percutaneous procedures including treatment of valvular heart disease, aortic dissections, dysrhythmias, and management of shunts for dialysis patients can also be performed using catheter systems. Further, complex aneurysms in the brain and other locations are increasingly being treated through a percutaneous endovascular route.

It is known that when a patient experiences a significant ischemic stroke event, those portions of the brain distal to the occlusion that experience a dramatic reduction in blood supply will affect the functioning of large regions of neurons. This reduction in blood supply may cause the patient to become symptomatic, cause the death of regions of the brain and/or put regions of the brain at the risk of dying if not treated quickly. Depending on the location and size of the occlusion will result in a wide range of symptoms in the patient and depending on the severity will ultimately determine how a physician may choose to intervene or not.

Time delays in effecting treatment will typically result in the death of a greater number of neurons. Table 1 shows that in the specific case of acute ischemic stroke, the pace or rate of neural circuitry loss in a typical large vessel supratentorial acute ischemic stroke can be very rapid.

TABLE 1

| Estimated Pace of Neural Circuitry Loss in Typical Large Vessel, Supratentorial Acute Ischemic Stroke Estimated Pace of Neural Circuitry Loss in Typical Large Vessel, Supratentorial Acute Ischemic Stroke | | | |
| --- | --- | --- | --- |
| | Neurons Lost | Synapses Lost | Myelinated Fibers Lost | Accelerated Aging |
| Per Stroke | 1.2 billion | 8.3 trillion | 7140 km/4470 miles | 36 yrs |
| Per Hour | 120 billion | 830 billion | 714 km/447 miles | 3.6 yrs |
| Per Minute | 1.9 million | 14 billion | 12 km/7.5 miles | 3.1 weeks |
| Per Second | 32,000 | 230 million | 200 meters/218 yards | 8.7 hours |

The numbers presented above represent an average with it also being known that there is a high degree of variability in the above numbers generally depending on the available blood supply to the ischemic region through collateral channels. A number of factors including time delays in making a decision, time delays in commencing an endovascular procedure and delays during the procedure, any of which may only be in the order of only a few minutes, can have a significant impact on neural circuitry loss and ultimately patient outcome.

The recent paper "Analysis of Workflow and Time to Treatment and the Effects on Outcome in Endovascular Treatment of Acute Ischemic Stroke: Results from the SWIFT PRIME Randomized Controlled Trial" (Radiology, accepted for publication Feb. 24, 2016), and incorporated herein by reference, quantitatively shows that there is a definitive improvement in patient outcome through fast reperfusion. In particular, this study concluded that "aggressive time goals may have contributed to efficient workflow environments". Further, the study quantifies inter alia that functional independence of a patient was significantly higher when treated quickly (i.e. within 2.5 hours of stroke onset).

Importantly, it is now known that efficient workflows during a recanalization procedure (of which the effectiveness and efficiency of a procedure is important) provides better outcomes.

Initially, in diagnosing ischemic stroke to assess possible treatments, it is important for the physician to know where the vessel occlusion is, how big the occlusion is, where any dead brain tissue (termed "core") is and, how big and where is the brain tissue that may have been affected by the ischemic event but that may potentially be saved (termed "penumbra").

The penumbra is tissue around the ischemic event that can potentially stay alive for a number of hours after the event by the perfusion of this tissue by collateral arteries. The collateral arteries may provide sufficient oxygen, nutrients and/or flushing to the penumbra tissue to prevent this tissue from dying for a period of time.

When responding to acute ischemic stroke, endovascular treatment of acute ischemic stroke due to large vessel occlusion in the anterior circulation is now the standard of care for patients under certain criteria. That is, patients exhibiting particular symptoms (i.e stroke symptoms of a particular severity) will benefit from early and rapid endovascular intervention to open occluded blood vessels. Generally, during various endovascular treatments, an interventionist will advance a series of catheters from the patient's groin through the femoral artery, descending aortic artery, to the aortic arch and into the cervical and cerebral arterial system towards the clot. After access to the clot is achieved by placement of the catheters, clot-retrieval and/or clot-suction devices are deployed through the catheter where the clot is either withdrawn and/or aspirated from the clot site.

There are many anatomical and situational considerations that can affect the severity and ultimately treatment of ischemic stroke. Importantly, as described above, while a blood clot may severely affect blood flow to the ischemic area, some blood flow may get to the ischemic area if collateral arteries are functioning to at least partially perfuse the affected area.

The most common large vessel occlusion that is treated by endovascular techniques is the M1 segment of the middle cerebral artery (MCA). When a patient has an M1 occlusion, the territory supplied by the M1 receives a dramatic reduction in blood supply. As a consequence distal neurons don't function well and the patient becomes symptomatic.

Recanalization procedures utilize a wide range of equipment and techniques to access a clot and effect its removal. Generally, the endovascular surgeon will have a number of tools at their disposal including a wide range of guide catheters, balloon guide catheters, diagnostic catheters, microcatheters, microwires, stents and other tools that individually have properties, features and functions that are effective for different procedures and patient presentations.

Typically these procedures are performed by gaining access to the arterial vascular system through the patient's groin area by puncturing the common femoral artery. An arterial sheath is inserted.

Then, under fluoroscopic (Xray) guidance, a catheter system (usually a co-axial system including a guide catheter or balloon guide catheter and diagnostic catheter) is advanced through the descending aorta to reach the aortic arch.

The diagnostic catheter is shaped and is used to hook the vessel of interest and with the help of a guidewire, the diagnostic catheter is advanced to the relevant carotid artery. Subsequently the guide catheter/balloon guide catheter) is advanced over the diagnostic catheter such that the tip is in the relevant internal carotid artery.

At this stage, the diagnostic catheter and wire are removed.

Subsequently, catheters that are designed for intracranial access are advanced through the guide catheter. This will typically consist of one of two approaches:
  a. a microcatheter and a microwire or
  b. a tri-axial system comprising of a distal access catheter (DAC), a microcatheter and a microwire.

For approach a: once the clot has been crossed by the microcatheter and microwire, the microwire is removed and a stent-retriever is slowly deployed across the clot. While aspirating through the guide catheter (with the balloon inflated if using a BGC) the stent-retriever is withdrawn to capture the clot and establish reperfusion.

For approach b: the DAC is placed proximal to the clot. In approach b1: the microcatheter is used to cross the clot and after removal of the microwire, a stent retriever is deployed. Then the stent-retriever and DAC are typically withdrawn together, while aspirating from the DAC. In approach b2: a stent retriever is not used and directly an attempt is made to capture the clot by aspirating through the DAC.

All of these approaches require accessing the carotid artery through the aortic arch.

It is known that stroke typically affects the elderly and with increasing age, there is an increase in tortuosity of the aortic arch making it tough to access the carotid artery. In particular, a highly tortuous combination of aortic arch and carotid artery can be difficult to advance catheter systems through as high bend angles and friction may cause catheters to prolapse into the ascending aorta and thus fail to advance through the desired vessel. In other words, when pushing a catheter system through tight bends, the system will always seek the path of least resistance and can end up being pushed in a wrong direction.

Catheter Performance

As mentioned above, there are generally two classes of catheters used in cerebral procedures namely diagnostic and guide catheters. Diagnostic catheters are generally those used to gain access to an area of interest whereas guiding catheters are used to support and guide additional equipment including diagnostic catheters, guidewires, balloons, other catheters etc. as may be required for a particular surgical technique.

Typical diagnostic catheters will range from 4 F to 6 F (French) and have lengths of 65-125 cm. They may have braided wall structures and they will generally have a soft tip with a range of shapes formed into the tip.

Guide catheters are generally larger (e.g. 6-8 F) and are 80-100 cm in length. They generally have reinforced construction with a significantly stiffer shaft to provide back-up (i.e. retro) support for the advancement of any additional equipment as listed above.

From an anatomical perspective, catheters generally pass through different zones of the vasculature, namely the abdominal and thoracic vasculature between the femoral artery and aortic arch (approximately 50-75 cm), the cervical vasculature (approximately 15-20 cm) and the cephalic/cerebral vasculature (approximately 10-15 cm). The vessels progressively narrow from 2 cm in the aorta down to 3 mm and smaller in the cerebral vessels.

Various properties and geometries may be engineered into both diagnostic and guide catheter including:

a. Trackability—the ability of the catheter to slide over a guide wire particularly through tortuous (tightly curved) vessels.

b. Pushability—the ability to advance the tip or head of the catheter based on the input from the operator from the hub (i.e. from outside the body).

c. Torquability—the ability to steer the tip of the catheter based on twisting at the hub by the operator.

d. Tip or head shape—the shape of the tip or head of the catheter will assist the operator in navigating the distal tip of the catheter through particular anatomical features. For example, a diagnostic catheter may have a flush, straight, simple curve, complex curve, reverse curve or double curve shape inter alia. Such shapes may be categorized as simple or complex.

e. Stiffness—the ability of a catheter to bend around a curve and support a catheter moving within it.

In particular, and as noted above, diagnostic catheters are provided with a wide range of tips having the above shapes to allow the interventionist a choice of tip shape when conducting a procedure mainly to address variations in a patient's anatomy.

Catheter Construction

Each catheter may be constructed from a plurality of materials, having various structures and/or layers within the catheter wall structure to give the catheter particular properties or functional characteristics. These may include:

Surface Coatings—Surface coatings desirably reduce thrombogenicity, have low friction coefficients and/or anti-microbial characteristics.

Reinforcement—Internal wire braiding is used to impart torque control/stiffness characteristics to the catheter.

Polymer Layers—Different polymers may be used to give different structural characteristics to the body of the catheter. For example, Polyurethanes can be soft and pliable and hence follow guide wires more effectively. However, they have a higher coefficient of friction.

Nylon may be used for stiffness and be able to tolerate higher flow rates of fluids through them.

The choice of a particular catheter or system of catheters may be determined by the skill and experience of a particular interventionist.

Some typical properties of different catheters are summarized in Table 2.

TABLE 2

| | | Summary of Catheter Properties | | |
|---|---|---|---|---|
| Catheter | Body Properties | Diameter | Typical Length | Typical Tip Features |
| Guide Catheter | Usually quite stiff Atraumatic tip Supports and guides other catheters Double lumen if Balloon Guide Catheter (BGC) | 6-8 F | Extracorporeal + Groin to Carotid 80-100 cm | May have balloon |
| Diagnostic Catheter | Variable Tip Stiffness Variable Tip Shapes Torquable | 4-6 F | Extracorporeal + Groin to Carotid 100-125 cm | Soft Tip Multiple Shapes |
| Microcatheter | Soft Tip Pushable Trackable | 1-5-2.5 f | Goes through the guide catheter Travel to intracranial vessels (over a microwire) and to beyond the clot. 150 cm | Rounded Soft Tip |
| Guide Wire | Pushable Torquable | 1 F | Travels inside of diagnostic catheter or guide catheter (used to advance these catheters to the cervical carotid artery) 150-300 cm | Rounded |
| Reperfusion Catheter | Multizone (may be up to 12-15 zones) Increasing level of softness distally to allow the catheter to negotiate significant tortuosity and remain atraumatic | 4-6 F (diameter may be more proximally to allow for better suction. | Travel inside the guide catheter. Usually over a microcatheter Extracorporeal + Groin to Occlusion 105-125 cm | Rounded Soft Tip Challenging design to prevent ovalization during passing through significant curvature and while |

TABLE 2-continued

| | | | | |
|---|---|---|---|---|
| Catheter | Body Properties | Diameter | Typical Length | Typical Tip Features |
| | Distal transition zones may extend for 30-40 cm) Enables two-way Fluid Flow Pushable | | | applying suction. |
| Stent | Integrated Clot Retrieval System Pushable | very small in its collapsed state (travel through microcatheter). In expanded state: 3-6 mm | Extracorporeal + Groin to Occlusion 180 cm Travel through microcatheter. | Integrated Clot Retrieval System |
| Microwire | Pushable Torquable 10-16/1000 of an inch soft atraumatic tip | 180-200 cm travels through microcatheter | extracorporeal to intracranially (beyond the clot) | round soft tip. |

Typical Endovascular Procedures for Treatment of Ischemic Stroke

As noted above, when an endovascular surgeon begins a procedure, access to the vasculature is typically obtained through the groin. After groin puncture, a variety of the following steps are performed to advance different catheters through the vasculature to a site of interest. Typically, in the case of a procedure using a balloon guide catheter and stent (i.e a clot retrieval device), these steps include:

Step A—Aortic Arch Access
a. Following groin puncture, a sheath is deployed. The sheath acts as an access port to the body and will be inserted about 5 cm of a typical 15 cm length into the femoral artery. The sheath has an ID of approximately 8 F.
b. An assembly of a guide catheter (GC)/balloon guide catheter (BGC), a diagnostic catheter (DC) and guide wire (GW) is advanced to the aortic arch. The GC/BGC will typically have an OD of 8 F.
The DC (OD 4-6 F) is retained inside the BGC and the GW (OD 0.035") is retained within the DC.

Step B—Carotid and Cerebral Artery Access
c. The DC is manipulated to gain access to the desired carotid artery.
d. After gaining access to the carotid artery, the GW is advanced, typically up to 20-30 cm towards the occlusion site (but within the cervical carotid arteries).
e. After the GW has been advanced (or concurrently and/or sequentially), the DC is advanced over the GW to gain access to the occlusion site. This may occur in a concurrent and/or sequential process depending on the particulars of a particular patient. However, this step can have significant problems. The design of the DC is to enable hooking the relevant vessel. Typically the tip (distal 5 cm) is pre-shaped and overall the diagnostic catheter is stiff and torquable. These properties make it possible to hook the vessel but actually work against the interventionist as one proceeds to advance the DC over the wire as often the whole system prolapses into the ascending aorta. An alternative approach is to not advance the DC but instead advance the BGC while leaving the DC in position at the origin of the vessel. This solution does work sometimes but often also has the same problem due to the stiffness of the guide catheter.

Step C—Guide Catheter (GC)/Balloon Guide Catheter (BGC) Placement
f. The GC/BGC is advanced over the DC and GW to also gain access to a straight segment of the cervical internal carotid artery.
g. The DC and GW are then fully removed.

Step D—Microcatheter/Microwire Placement
h. A microcatheter (MC) and microwire (MW) are advanced together through the BGC all the way to the clot such that the distal tip of the MC and MW are positioned just past the distal edge of the clot. A MC as described in Applicant's copending application U.S. Ser. No. 14/809,867 and incorporated herein by reference, may be used to effect movement through these arterial systems.
i. Once the MC is positioned, the MW is removed.

Step E—Stent Deployment
j. A stent (i.e. clot retrieval device) is advanced through the MC until the distal tip of the stent is adjacent the distal end of the MC.
k. The stent is unsheathed by pulling back on the MC while holding the stent in position. As the stent is unsheathed it will expand into clot to engage with the clot.

Step F—Clot Removal
l. The BGC is inflated to stop antegrade flow and retrograde flow (suction) through the BGC is initiated.
m. Simultaneously, the stent which is now engaged with the clot, together with the MC is pulled proximally through the BGC to outside of the body.
n. A check angiogram is performed through the BGC to see if the clot retrieval has been successful. If not the steps j-m may be repeated again.
o. Once successful reperfusion has been achieved the BGC, stent and clot are removed from the body.

US 12,629,161 B2

9                                                                      10

Variations

In variations of the procedure, a distal access catheter (DAC) (4-6.5 F) may be added to the procedure. This can be done one of two ways a. Aspiration technique.
  i. In this technique, after access to the cervical internal carotid artery has been achieved using a guide catheter and DC, the guide catheter (GC) which is not a BGC (i.e. a DAC) is placed in the cervical internal carotid artery.
  ii. The DC is removed
  iii. A tri-axial system consisting of a DAC, a MC and MW are advanced towards the intracranial circulation with the aim of having the tip of the DAC (Aspiration catheter) reach the face of the clot. For achieving this it is possible that the MC and MW may have to be placed beyond the clot.
  iv. The MW and MC are removed.
  v. With the DAC at the face of the clot, suction through the DAC is applied until there is successful retrieval of clot or the endovascular surgeon decides to try an alternative approach.

Local suction has an advantage that more of the suction pressure is likely to be transmitted to the clot.

b. Solumbra technique
  i. The initial part of this technique is the same as the Aspiration technique (i.e steps a(i)-a(iii)).
  ii. However once the MC is beyond the clot and the DAC is at the face of the clot, the MW is removed and a stent is deployed across the clot.
  iii. Then, while applying suction to the DAC, the MC and stent are withdrawn. Thus, the suction pressure is right next to the clot rather than from the neck as with a BGC. Also, the stent enters the DAC while still in the intracranial vessels thus reducing the likelihood of losing the clot once it has been captured.

In cases where the aspiration techniques without using a stent are not successful in removing the clot, with a BGC in place, a GW, MC and stent may be subsequently deployed.

While the above procedures are effective, there is a need for catheter systems that make it easier to access the carotid artery in the presence of a tortuous aortic arch and reduce the number of steps in any procedure such that the procedure can be completed in a shorter time period. In particular, there has been a need for improved catheter systems that have a wider range of physical properties that reduce the need to withdraw catheters from the body and insert other catheters.

SUMMARY OF THE INVENTION

In accordance with the invention, there are provided systems and methods for improving the efficiency of surgical procedures and easier access to the relevant carotid artery in the presence of a tortuous aortic arch using catheter systems to move from an entry point to a location in the body where a treatment or diagnostic procedure may be completed. The system enables an interventionist to effectively advance a plurality of catheters, in a manner that successively builds the appropriate amount of stiffness and support within a catheter system so as to minimize the risk and/or allow the interventionist to prevent prolapse of the system into the ascending aorta. In other words, the system, by the combination of concentric catheters and the relative properties of each catheter allows the interventionist to efficiently advance catheters where the interventionist has a greater number of options to negotiate tight corners within the vasculature while still gaining access to the cerebral vasculature within an efficient time window.

In another aspect, the invention provides a more efficient procedure to gain cerebral access beyond a tortuous aortic arch by reducing the number of total steps for an endovascular procedure by having a G2B catheter in position for intracranial access as soon as access to the carotid artery in the neck is successful.

More specifically, the invention provides an endovascular system of catheters for use in an endovascular procedure for gaining access to cervical arteries and treating intracranial and cervical vascular conditions, the endovascular catheters for placement within the human vasculature between the groin and cerebral arteries comprising:

an outer guide catheter (GC) having a length sufficient to extend from the groin to the internal carotid artery;
a groin to brain catheter (G2B) enabling aspiration through the G2B catheter and having:
  a diameter to fit and slide within the outer guide catheter;
  a length longer than the outer guide catheter and having a length sufficient to reach an intracranial clot;
  a soft distal tip region having a length sufficient to extend from the cervical internal carotid artery of a patient to cerebral arteries of a patient; and
  a proximal region having a length sufficient to extend from the carotid artery of a patient to outside the patient through the groin;
a diagnostic catheter (DC) having a diameter to fit and slide within the G2B and having a pre-shaped tip for accessing varying anatomies of an aortic arch and having a length longer than the G2B;
a guide wire (GW) having a diameter to fit and slide within the DC and having a length longer than the DC;
where the soft distal tip region of the G2B has sufficient flexibility to ride over a DC without causing prolapse of a DC positioned at or beyond the aortic arch;
and where the outer GC has a stiffness enabling the outer GC to ride over the G2B without causing prolapse of the G2B and DC when the G2B and DC are positioned at or beyond the aortic arch.

In various embodiments:
a. the distal tip region of the G2B has a length of 10-20 cm;
b. the G2B proximal region has a length of 85-120 cm; and/or
c. the stiffness of the G2B proximal region is greater that the stiffness of the G2B distal tip region;

In another embodiment, the system includes a second GW having a stiffness greater than the stiffness of the GW.

In one embodiment, the guide catheter is a balloon guide catheter.

In one embodiment, the system further includes a pump for operative connection to a proximal end of the G2B, the pump enabling antegrade flow through the G2B to assist in maintaining antegrade circulation pressure during intracranial access and retrograde flow through the G2B after a clot has been accessed and during clot aspiration.

In another aspect, the invention provides an endovascular method for gaining access to cervical arteries and treating intracranial and cervical vascular conditions, the endovascular method for placement a catheter system within the human vasculature between the groin and cerebral arteries comprising the steps of:
a. introducing a quadra-axial catheter system as described within through a groin puncture;
b. advancing the catheter system to the descending aorta;

c. advancing the GW and DC to a desired carotid artery and manipulating the GW into the desired carotid artery;

d. advancing the GW to the cerebral arteries;

e. advancing the G2B over the GW and DC to the cerebral arteries;

f. advancing the GC over the G2B to the base of the skull; and, g. withdrawing the DC and GW.

In one embodiment, step d includes advancing the GW and DC to the cerebral arteries prior to step e.

In one embodiment, step e includes the step of removing the GW and introducing a second GW having a stiffness greater than the GW prior to step f.

In one embodiment, after step d, the method includes withdrawing the DC and introducing a DC having a different tip region prior to step e.

BRIEF DESCRIPTION OF THE DRAWINGS

Various objects, features and advantages of the invention will be apparent from the following description of particular embodiments of the invention, as illustrated in the accompanying drawings. The drawings are not necessarily to scale, emphasis instead being placed upon illustrating the principles of various embodiments of the invention; however, the scale of the drawings may be relied upon for supporting the relative position of described components with respect to one another. Similar reference numerals indicate similar components.

FIGS. 3A, 3B and 3C are schematic cross sections of a distal access catheter (DAC) showing different construction features in accordance with the prior art.

FIGS. 4A and 4B are schematic cross sections of a balloon guide catheter (BGC) showing an un-inflated and inflated configuration in accordance with the prior art.

FIG. 6 is a diagram showing features of a groin to brain catheter in accordance with the invention.

FIG. 8A shows a GC and G2B in position in the descending aorta and a DC and GW in position to hook a carotid artery. FIG. 8B shows the GW and DC advanced to the base of skull level with the GC and G2B in the descending aorta. FIG. 8C shows the G2B advanced to the base of skull level with the GC in the descending aorta. FIG. 8D shows the GC advanced to the base of skull level with the DC and GW removed.

DETAILED DESCRIPTION OF THE INVENTION

Introduction

With reference to the figures, catheter systems and methods of deploying those catheter systems are described.

Figure 1:
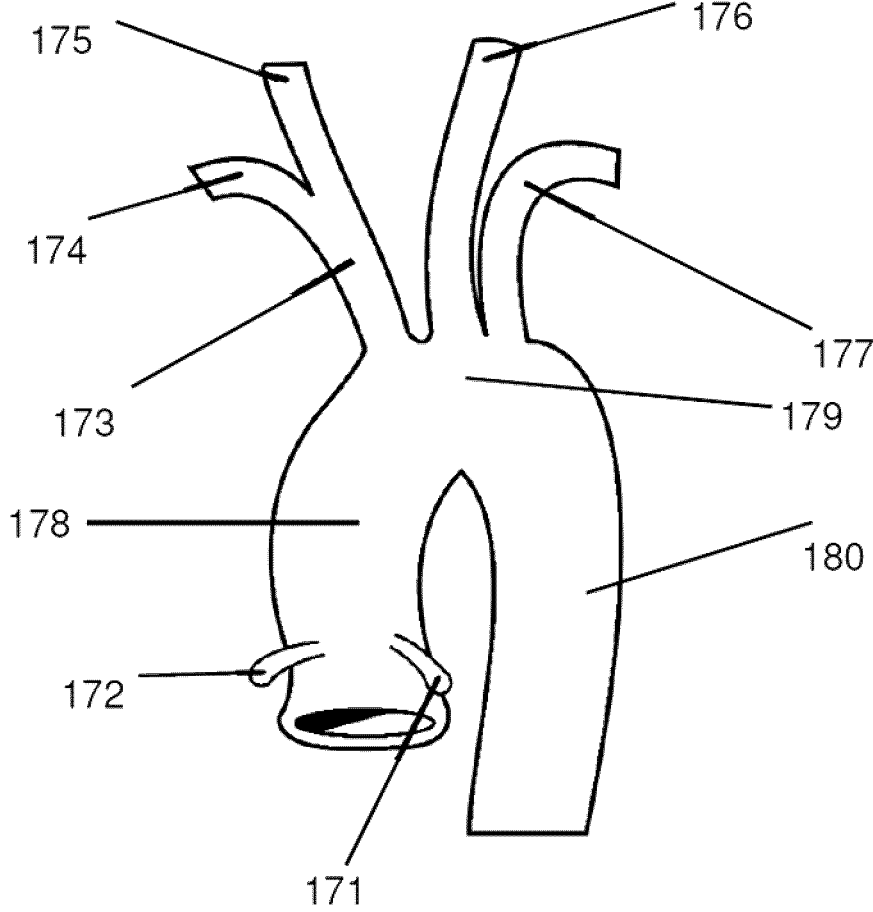
FIG. 1 is a schematic sketch of an aortic arch and associated blood vessels.

By way of background, FIG. 1 shows a typical aortic arch 179 and various connecting vessels of the human vasculature. The aortic arch 179 is connected to the ascending aorta 178 and the descending aorta 180. The ascending aorta is connected to the right and left coronary arteries 171, 172. The aortic arch is connected to the brachiocephalic artery 173 which splits into the right subclavian artery 174 and the right common carotid artery 175. Also connected to the aortic arch are the left common carotid artery and the left subclavian artery 177.

In a typical endovascular procedure utilizing one or more catheters as described above, the interventionist/surgeon navigates various catheters up the descending aorta 180 from the femoral artery and into the aortic arch 179 and into the left common carotid artery 176.

Figure 1A:
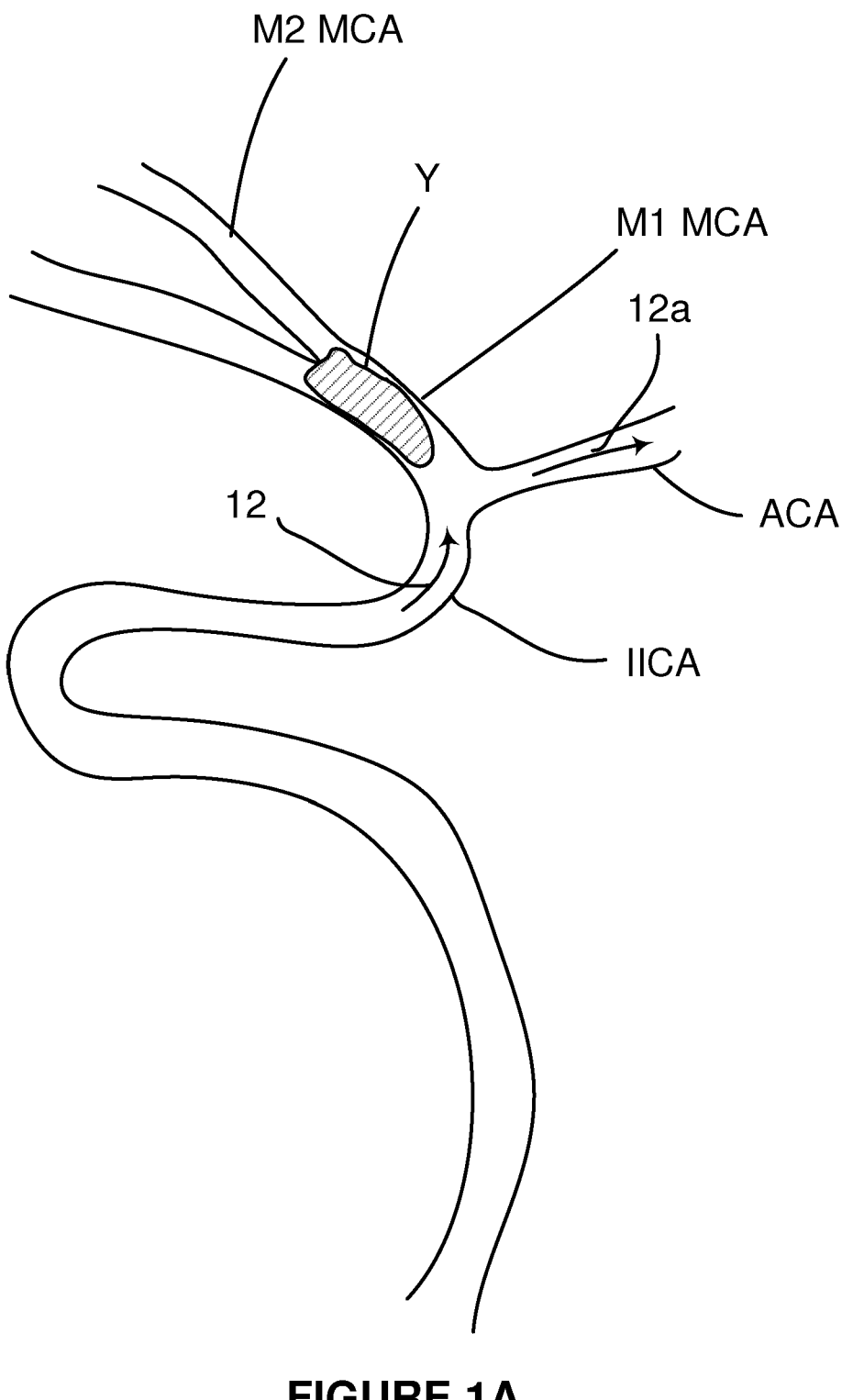
FIG. 1A is a schematic sketch of a portion of brain vascular anatomy showing the ophthalmic artery (OA), intracranial internal carotid artery (MCA), anterior cerebral artery (ACA), M1 segment of the middle cerebral artery and M2 segment of the middle cerebral artery.

FIG. 1A is a schematic diagram of brain vascular anatomy showing the intracranial internal carotid artery (MCA), anterior cerebral artery (ACA), M1 segment of the middle cerebral artery and M2 segment of the middle cerebral artery. A clot Y is shown within the M1 MCA with arrow 12 showing the direction of blood flow prior to any procedure. Blood flow as shown by arrow 12a through the ACA is supporting collateral perfusion to affected areas of the brain.

Figure 2:
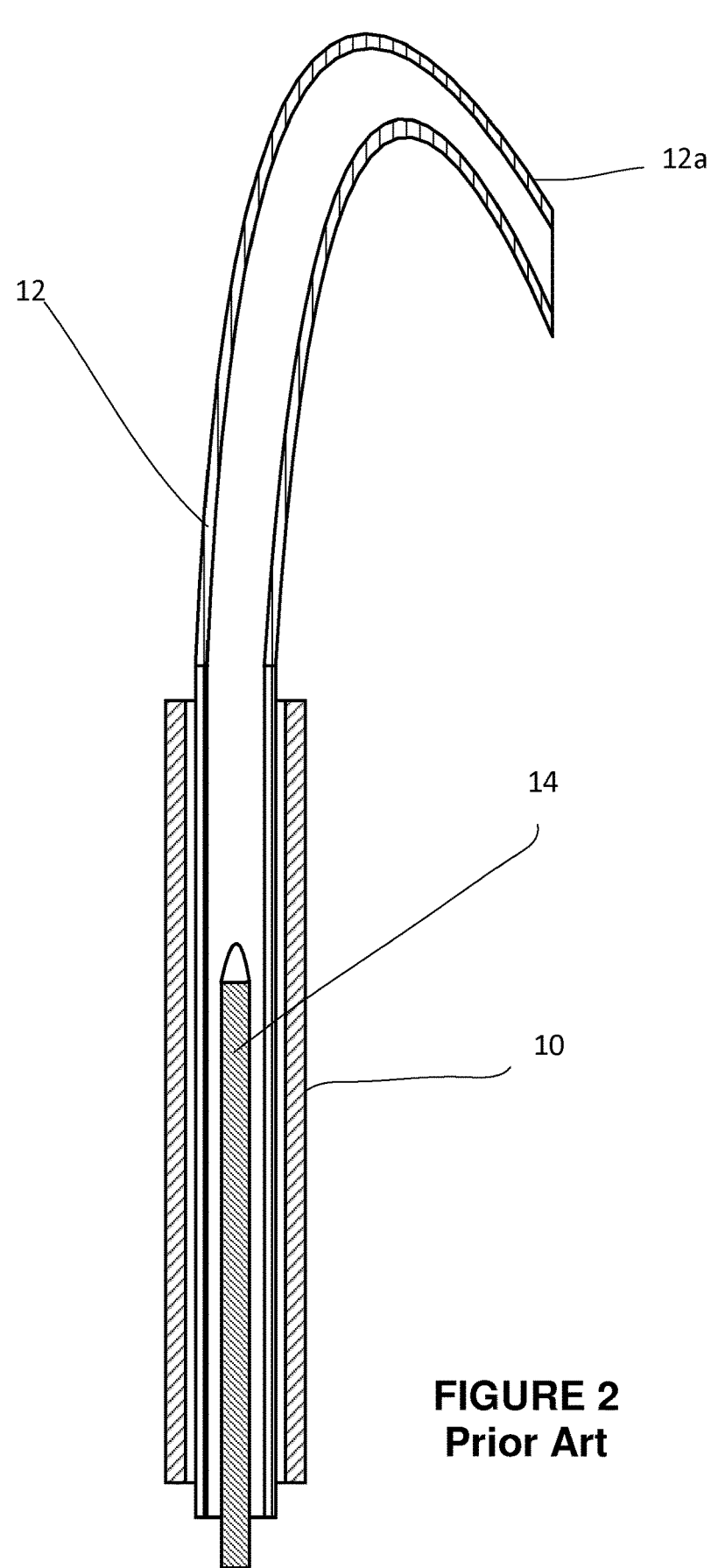
FIG. 2 is a schematic cross section of a guide catheter, diagnostic catheter and guide wire in accordance with the prior art.

By way of further background, FIG. 2 shows a schematic cross section of a prior art tri-axial system of a guide catheter GC 10, a diagnostic catheter DC 12 and guide wire GW 14. As known, the DC has a soft, pliable tip 12a having a pre-formed shape that can be manipulated into and through the cervical arteries.

Figure 2A:
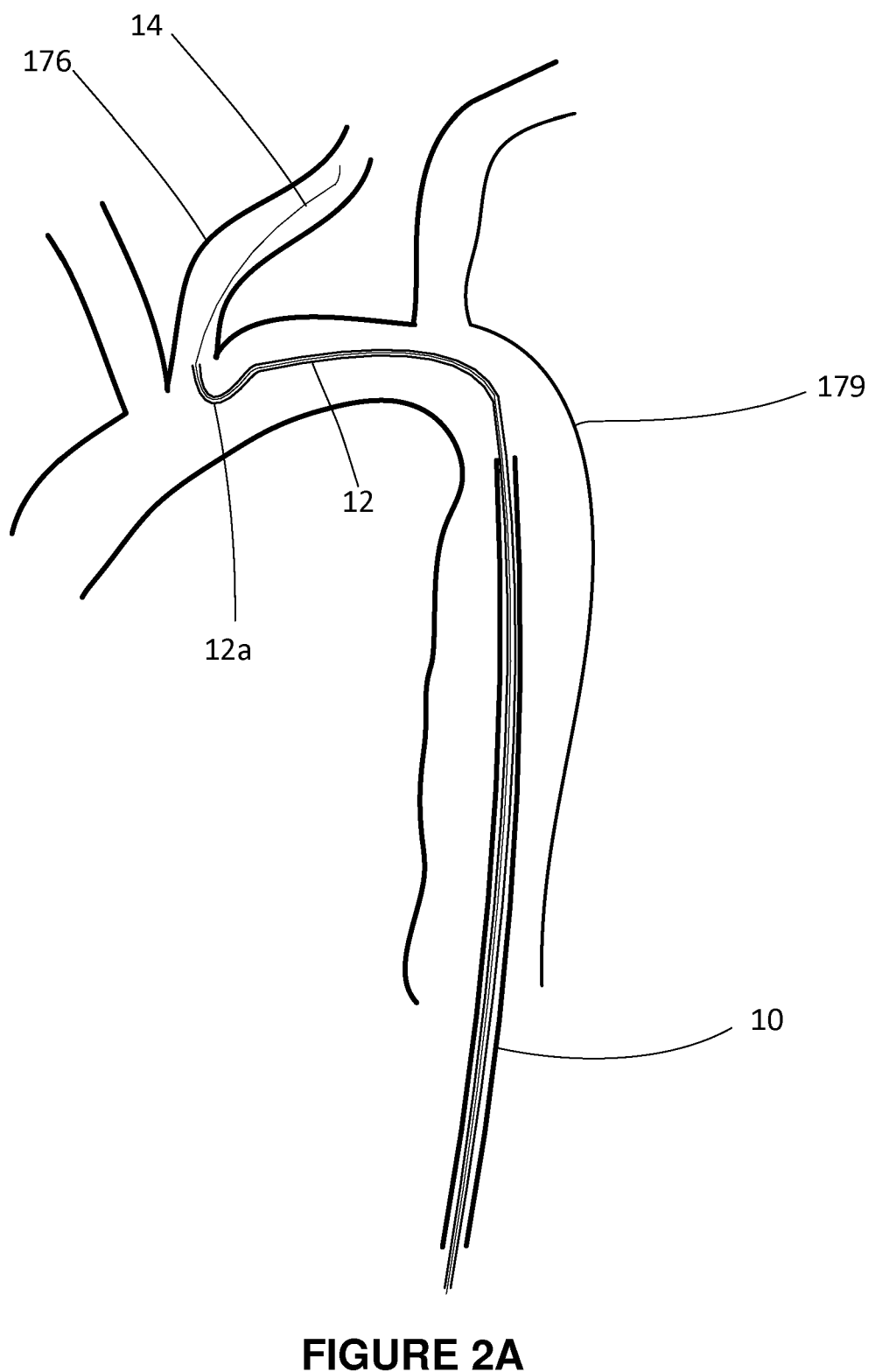
FIG. 2A is a schematic diagram of a guide catheter, diagnostic catheter and guide wire being maneuvered into the internal carotid artery in accordance with the prior art.

FIG. 2A is a schematic diagram of a tri-axial assembly of a GC and a DC catheter and a GW that an interventionist may have chosen to gain access to the carotid arteries in accordance with the prior art. A DC, with an internal GW, is used to hook the left common carotid artery 176. In this case, the DC is shown having a complex curved tip 12a that was chosen by the interventionist due to the particular anatomy of the patient and his/her determination of the relative angles of the aorta and left common carotid artery with respect to one another. The GW is shown as advanced from the DC after access to the carotid artery was achieved.

As shown, primarily due to the stiffness of the GC, the GC is only advanced to the base of the aortic arch.

Figure 3A:
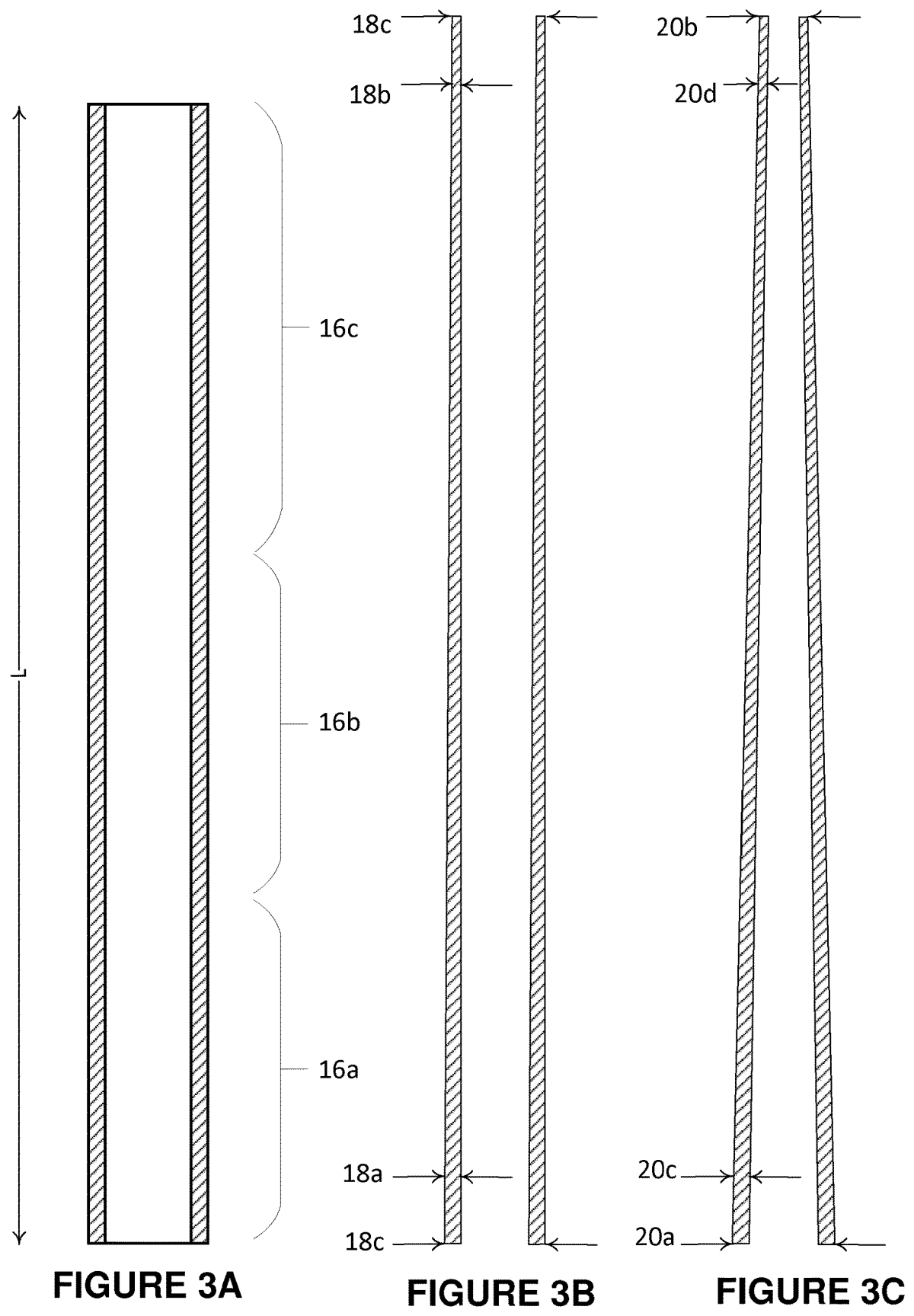

FIGS. 3A, 3B and 3C show schematic cross sections of other catheters and the structural and functional features that may be incorporated into them. For example, a catheter may include zones having different stiffness properties in different zones (e.g. 16a, 16b, 16c) (FIG. 3A). The wall thickness of a catheter may be different along the length of a catheter where the proximal wall thickness 18a is greater than the distal thickness 18b (FIG. 3B) and where the OD 18c of the catheter remains constant over the length. Further, the diameter of a catheter may vary along its length where the proximal diameter 20a is greater than the distal diameter 20b together with varying wall thicknesses 20c, 20d (FIG. 3C). Different zones within a catheter may be independently fabricated and assembled by known techniques including attaching individually formed sections together to form catheters having different properties across different zones.

The schematic cross section of the tip of a balloon guide catheter (BGC) 22 in an uninflated configuration 22a (FIG. 4A) and inflated configuration 22b (FIG. 4B) is also shown.

In accordance with the invention, a catheter system having a broader range of properties is described and, in particular, a catheter system having both guide and aspiration capabilities in a single catheter. As such, the catheter system can be effective in reducing the number of steps in a procedure and, hence be completed in less time. In addition, a system that improves the ability to advance catheters through a tortuous vasculature is described.

Figure 5:
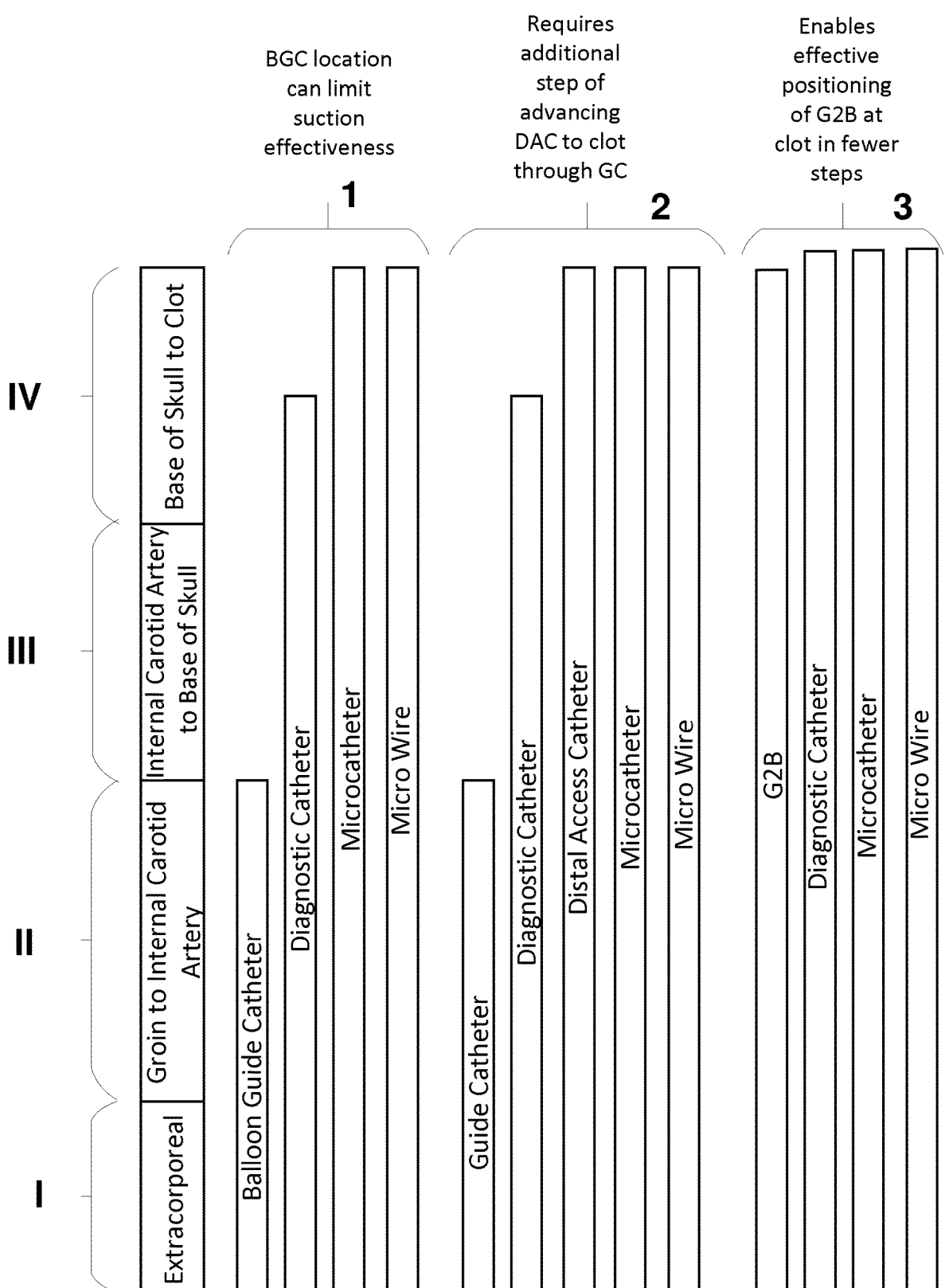
FIG. 5 is a diagram comparing various catheter systems used in different endovascular procedures with a comparison of catheter lengths.

With reference to FIG. 5, different catheters are outlined as bundles that may be utilized for endovascular procedures as described above. FIG. 5 shows the 4 main zones of operation of a catheter namely the extracorporeal zone I where the interventionist manipulates the proximal ends of individual catheters, the groin to internal carotid artery zone II, the internal carotid artery to the base of the skull zone III and base of the skull to the clot zone IV. As shown, past procedures may utilize different catheters to conduct the procedure. Procedure 1 is shown as a procedure utilizing a BGC, DC, MC and MW and Procedure 2 is shown as a procedure utilizing a GC, DAC, DC, MC and MW. In both of these procedures, either a GC or a BGC is advanced to the ICA level which can provide particular disadvantages, namely possible suction problems with the BGC procedure (1) or additional steps/time with the combination GC/DAC procedure (2)

As such, the subject invention provides the equipment and methodology to both improve suction effectiveness as compared to procedure 1 whilst reducing the steps/time as compared to procedure 2 by providing a groin to brain (G2B) catheter system that can effectively be advanced over a DC/MC/MW to the clot and that supports aspiration at the clot. In addition, the subject system enhances access from the aortic arch into the internal carotid artery particularly in situations where the aortic arch to internal carotid artery is tortuous.

Presently, as noted above the design of catheters and the methods of accessing a clot site requires that the guide catheter (with or without a balloon) is initially positioned in the descending aorta (Step A), followed by carotid artery access by the manipulation and advancement over the diagnostic catheter (Step B). This may be followed by the placement of the distal access catheter (Step C) after withdrawal of the diagnostic catheter and guide wire. This is then followed by microguide wire and microcatheter placement (Step D), and then followed by stent deployment (Step E) (optional) and clot removal (Step F).

In particular, time is required during step C to guide the BGC or DAC into position. As noted, in both techniques, there are limitations, namely in the case of a BGC, that the BGC cannot be advanced beyond the cervical regions and in the case of a DAC, the DAC requires support from a GC. For a BGC procedure, this lower placement can be problematic to suction and in the case of a DAC, this technique requires additional time to advance both the GC and DAC to their respective positions. In addition, there may be technical issues in advancing the BGC over the DC to get into the carotid artery (in the presence of tortuosity) due to the stiffness of the BGC. In particular, there is a high risk of prolapsing the BGC or DAC into the ascending aorta. That is, in some patients, the physician is unable to advance the BGC or DAC into the cervical arteries as the relative angles and stiffness of the arteries with respect to one another and stiffness of the catheters does not allow the catheters to slide over one another to advance but instead will collapse into the ascending aorta instead of bending into the carotid arteries.

It would therefore be desirable to enable the advancement of a combined guide catheter (GC) and an aspiration catheter (AC) (e.g. either a BGC or a DAC) to the occlusion site without the step of having to advance a DAC from outside the body through and out of the distal end of the GC and over a GW to the occlusion site.

Figure 7:
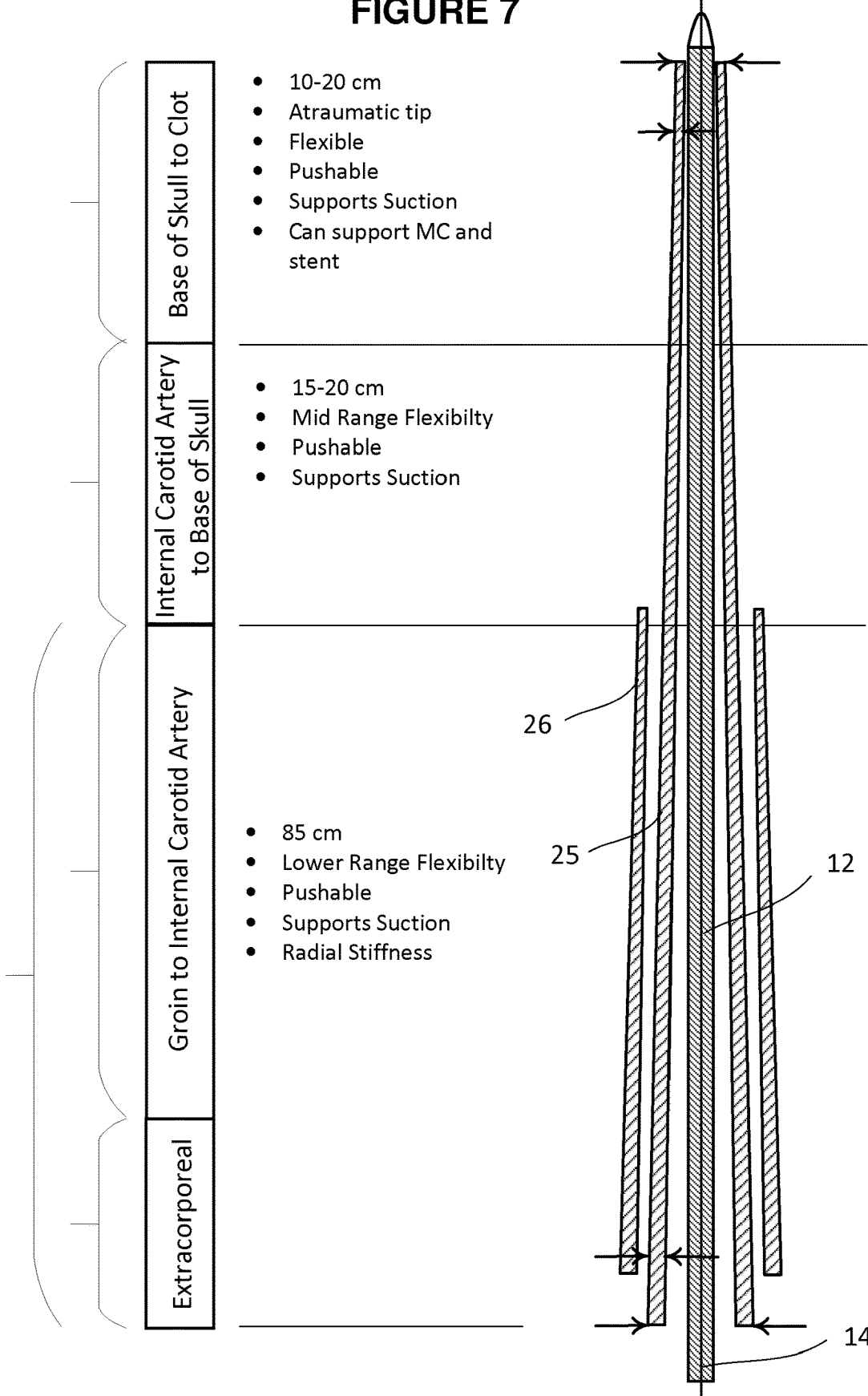
FIG. 7 is a diagram showing features of a groin to brain catheter system where the system includes an outer sleeve in accordance with one embodiment of the invention.

In accordance with the invention a G2B is described with features and properties as shown Table 3 and FIGS. 6 and 7. In addition, a kit having a DC designed to engage within a G2B is described.

TABLE 3

| G2B Features and Properties | | |
|---|---|---|
| Feature | Value | Comments |
| Overall Length | 120 cm | |
| TIP ZONE | | |
| Length | 20 cm | |
| End Anatomical Position | Cerebral arteries | |
| Axial Stiffness | Soft | Sufficiently pliable to enable movement through tortuous cerebral arteries |
| Distal Tip Diameter | 5.5-6 F | |
| Proximal Diameter (junction with mid zone) | 6 F | |
| Tip Edge | Rounded/ Atraumatic | |
| Opening | Semi-Rigid | Enables retrograde flow and recovery of clot |
| Radial Rigidity | Yes | Sufficient to enable retrograde flow |
| Axial Rigidity/ Compressibility | Yes | Sufficient to enable distal movement over MC/MW/DC with support |
| MID ZONE | | |
| Length | 15 cm | |
| End Anatomical Position | Distal cervical internal carotid artery | |
| Axial Stiffness | Medium | |
| Distal Junction Diameter | 6 F | |
| Proximal Diameter (junction with mid zone) | 6 F | |
| Radial Rigidity | Yes | Sufficient to enable retrograde flow |
| Axial Rigidity/ Compressibility | Yes | Sufficient pliability to negotiate the tortuosity of the neck vessels. However rigid enough that it doesn't recoil as the MW/MC are advanced through it and as the distal zone is advanced into the cerebral vessels. |
| PROXIMAL ZONE | | |
| Length | 85 cm | |
| End Anatomical Position | Extra-corporeal to Aortic Arch | |
| Axial Stiffness | low stiffness | |
| Distal Junction Diameter (junction with mid zone) | 6 F | |
| Proximal Diameter | 8 F | |
| Radial Rigidity | Stiff | Sufficient to enable retrograde flow |
| Axial Rigidity/ Compressibility | Yes | Sufficient to enable distal movement over MC/MW/DC without support |

Importantly, while the above table describes a G2B having three general zones, it is understood that each general zone in itself may have further sub-zones where properties such as diameters, axial stiffness, radial rigidity and wall structures may vary either in a step-wise, continuous or semi-continuous manner. Also, systems having similar properties in the mid and proximal zones may be utilized.

Deployment Method

Figure 8A:
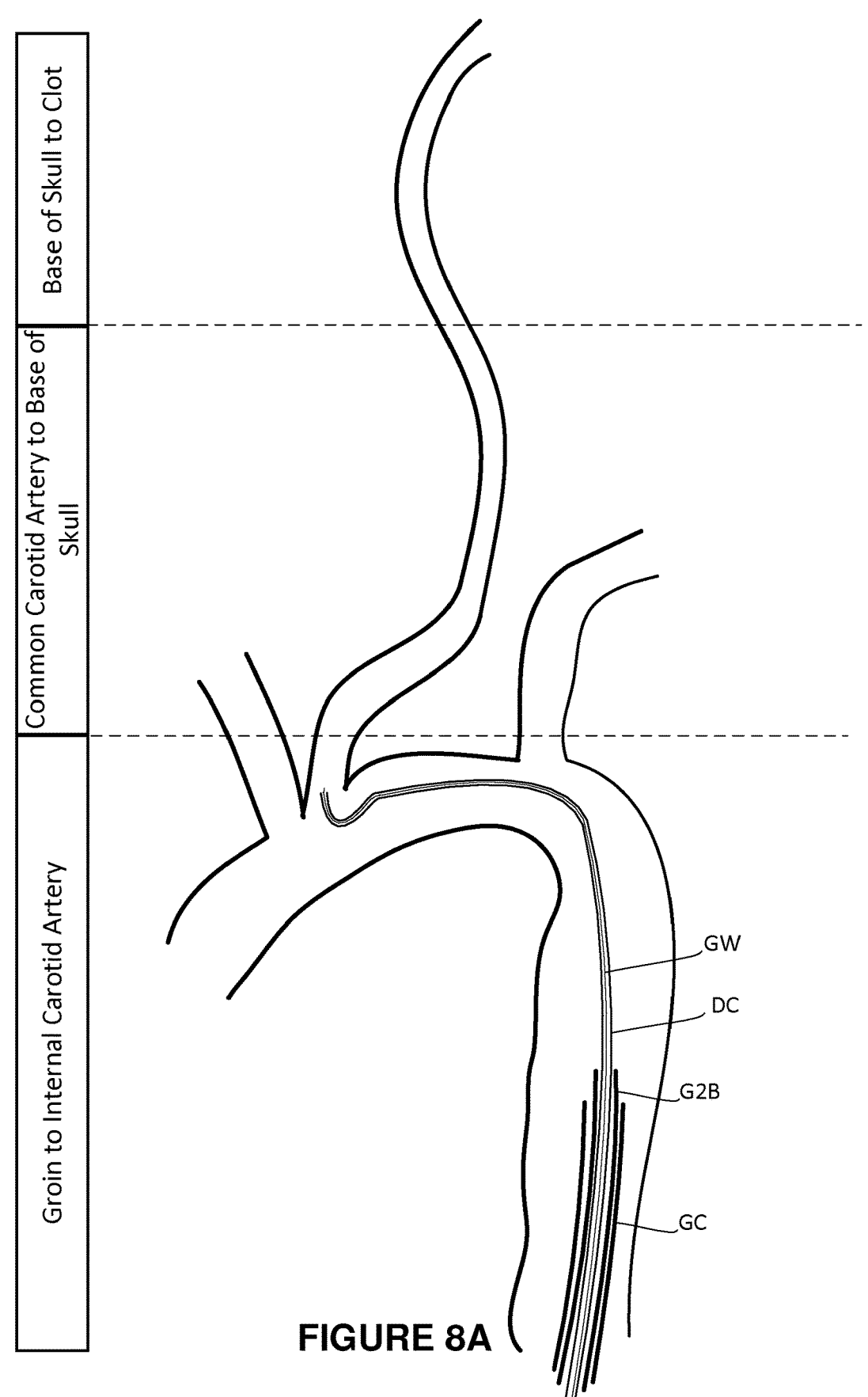
FIGS. 8A-8D are schematic diagrams showing the process by which a quadra-axial system may be advanced in accordance with one embodiment of the invention.

In accordance with methods of the invention, a procedure for introducing a modified G2B catheter as described (a G2B method) would be as follows and as shown in FIGS. 8A-8D:

As described above, aortic arch access (G2B step A) is similar involving the step of initially deploying a sheath. Thereafter, and external to the body, an assembly of a guide catheter (GC), a G2B, a diagnostic catheter (DC) and guide wire (GW) (typically 0.035") is prepared and advanced to gain access to the aortic arch. As shown in FIG. 8A, the GC is advanced to the descending aorta, the G2B a few centimeters past the GC and the DC and GW to the desired carotid artery. The GW is generally held at substantially the same position as the DC during the steps where access to the carotid artery is being obtained. During this step, the DC and GW are torqued, pushed and/or pulled in order to hook the tip of the DC into the desired vessel. When the DC/GW are in the desired vessel, by a combination of advancing the GW and DC, the two can be advanced to the base of the skull.

However in patients with significant tortuosity and especially when gaining access to the left common carotid artery, the DC may not advance over the GW. That is, a combination of the shape of the DC (which is necessary to hook the relevant vessel from the aortic arch) its stiffness and the angles of the vessels involved, when an attempt is made to advance the DC, the DC/GW combination has a tendency to prolapse into the ascending aorta.

Figure 8B:
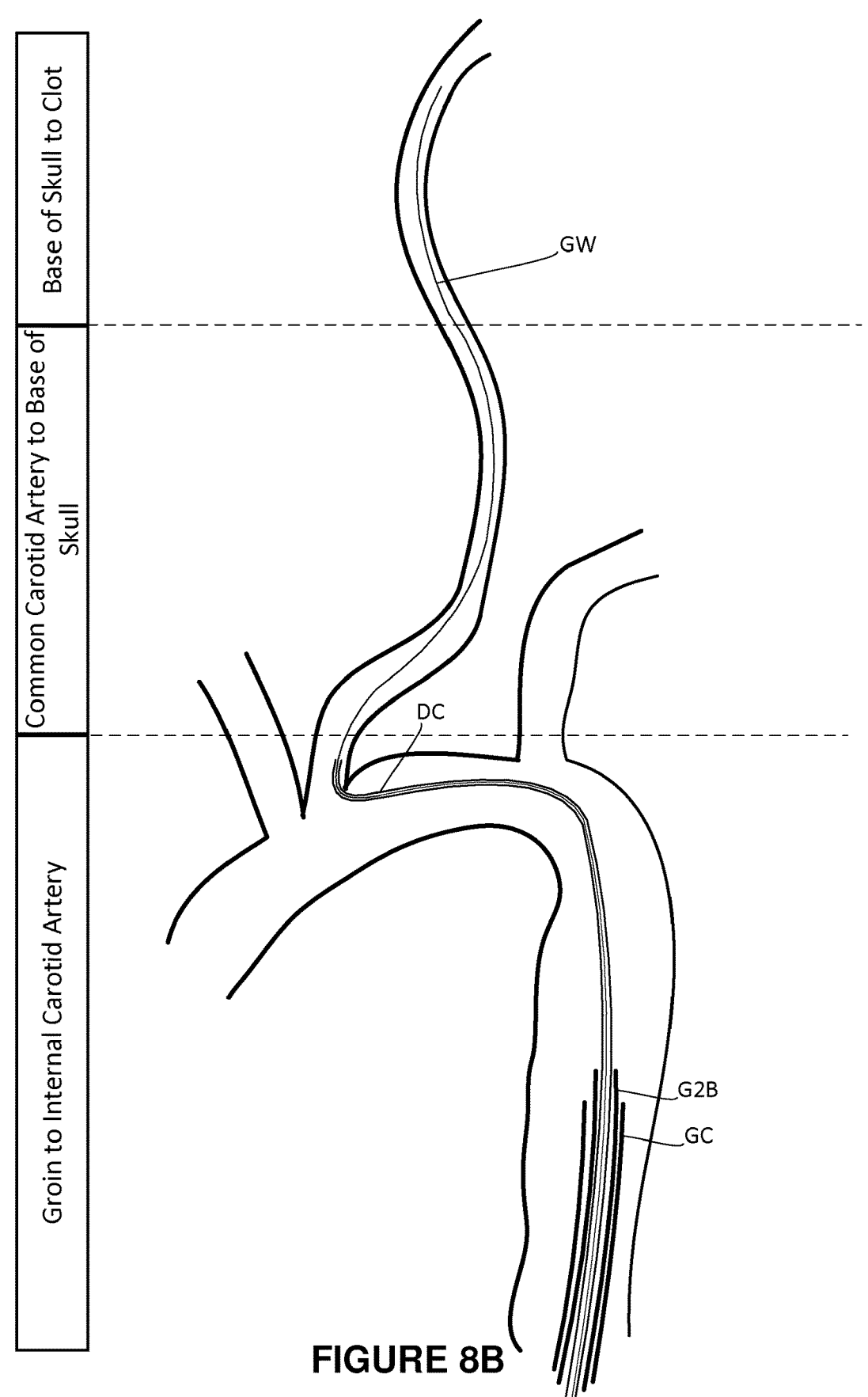
Figure 8C:
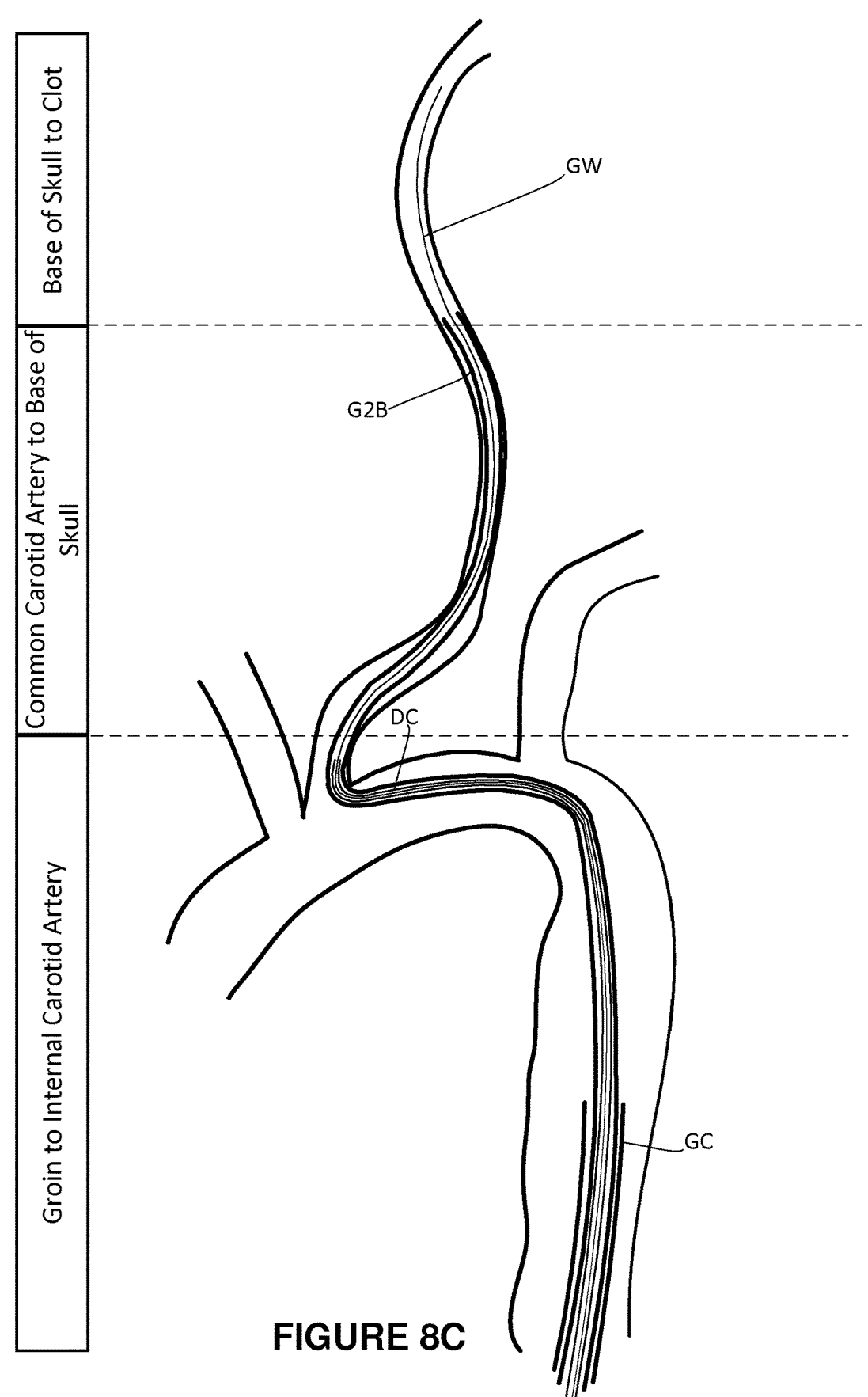

In such situations, the interventionist may choose to only advance the GW keeping the DC at the origin of the vessel in the aortic arch, rather than trying to advance the DC as shown in FIG. 8B. Thereafter, the G2B is advanced over the system such that the G2B reaches the cervical internal carotid artery. The soft tip and the lack of a pre-determined shape of the G2B makes it conducive to follow the GW as shown in FIG. 8C.

Once the G2B is in the internal carotid artery, the interventionist can have a few choices regarding next steps depending on the assessment of the particular situation:

a. Advance the DC (which now has a greater probability of going towards the internal carotid artery rather than the aortic arch since it is now traveling inside the G2B). Once this is successful, the GC can be advanced over the combination of G2B, DC, and GW. This option would be chosen as means of providing additional stiffness to the assembly to advance the GC.

b. Hold the DC at the aortic arch but instead advance the GC over the G2B and GW. If this is successful, the DC and GW can be removed. This procedure would be desirable to the extent that if successful would save time as the DC is not advanced.

c. If none of the above two are successful, the interventionist can pull out the GW and replace it with a stiffer GW (which is likely to follow the internal carotid artery since it will be traveling inside the G2B). With the support of the stiffer wire follow steps a or b as above. Generally, at this stage, if a failure is being detected, the interventionist would hold the G2B at its best position without failure which may enable a stiffer GW to be introduced.

d. If none of the above is successful, the interventionist can remove the DC and GW and replace it with a DC with a gentler curve and/or softer tip and a stiffer wire.

Since these are traveling inside the G2B, these are more likely to go to the internal carotid artery. Also since the tip of the DC is gentler, it is less likely to prolapse towards the ascending aorta.

FIG. 8C shows one situation where the interventionist has not been successful in advancing the DC to a position at the base of the skull but has been successful in pushing the G2B over the DC/GW also to the level of the base of the skull. Importantly, as the G2B has a soft tip, it will be generally have sufficient compliance such that it can readily ride over the DC/GW without causing the DC/GW to pull backwards particularly as the tip of G2B makes the tight turn into the desired artery. The soft tip, which may be approximately 20 cm and can thus be positioned at the base of the skull, thus creating in this case, a bi-axial system to the base of the skull. However, in some situations (not shown), the DC can be effectively advanced over the GW to the base of the skull.

Either way, after a stable situation has been created as determined by the interventionist, namely various combinations of GW/DC/G2B, the GC/BGC can be advanced. In other words, as the objective is generally to advance the GC/BGC to the base of the skull, the appropriate level of support must be available to enable the GC/BGC to negotiate the tight turn into the carotid artery.

As can be appreciated, the system gives the ability to the interventionist to progressively build up the necessary support to achieve the objective of placement of a GC/BGC at the base of the skull.

Figure 8D:
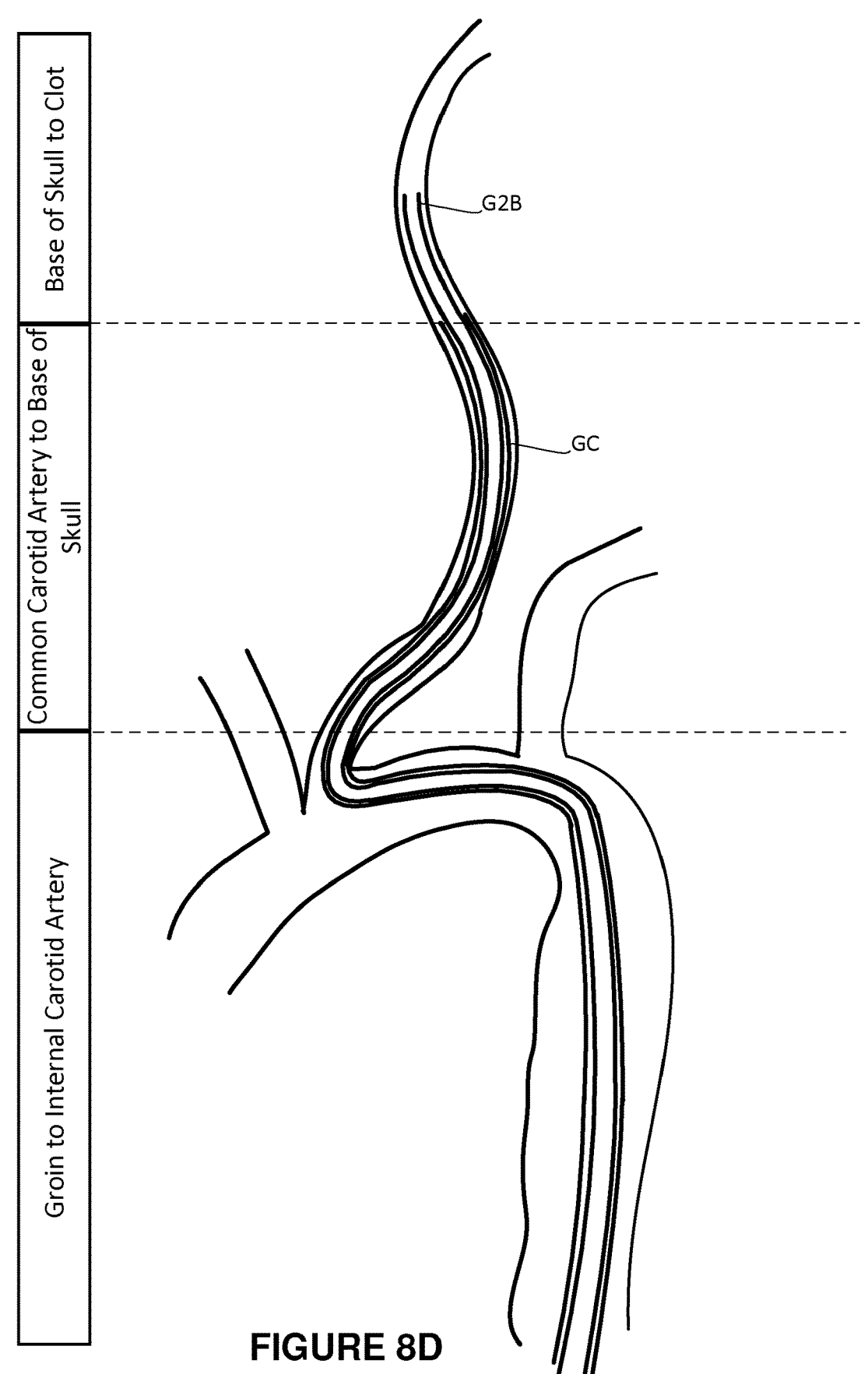

As shown in FIG. 8D, after the GC/BGC has been moved over the G2B to the base of the skull and the GW and DC have been removed, a direct conduit from the groin to the base of the skull has been created.

Thereafter, the interventionist can conduct a desired clot removal procedure by introducing a MC and stent retrieval and/or conducting an aspiration procedure through the G2B.

Thus, and in accordance with the invention, the quadra-axial system enable the additional G2B and GC to be moved further in the distal direction while decreasing the prolapse risk and ultimately providing a direct conduit to the site of a clot enabling different treatment options.

G2B Kit

In one embodiment, the kit includes a GC/BGC 26, a G2B 25, a DC 12 and GW 14 as shown in FIG. 7. In this embodiment, the kit may comprise a co-axial system (GC/BCG and G2B where the GC/BGC has a stiffness that provides support and stability to the G2B and has a length enabling it to be advanced to the base of the skull. As described above, the G2B is longer (to allow intracranial access) and softer (to allow navigability and the ability to ride over a DC/GW). The DC/GW would be placed inside the G2B making it a quadra-axial system and all four can be selectively advanced together. Once the G2B is in the desired position at or near the base of the skull, the diagnostic catheter could be replaced by a microcatheter as described above. Generally, the purpose of the GC/BGC is to provide continued access to the carotid artery in the event that the G2B must be withdrawn. For example, there are surgical situations where during clot removal the suction catheter (i.e. the catheter through which the clot is being withdrawn) may become jammed by the clot such that retrograde flow through the suction catheter to fully withdraw the clot is not possible. In this case, if the vessel hasn't been fully recanalized and as the GC is still in the carotid, the G2B can be quickly advanced to the clot again.

In another embodiment, the kit may include a pump for operative connection to a proximal end of the endovascular catheter to support both antegrade and retrograde flow through the endovascular catheter. In particular, antegrade flow through the endovascular catheter can be used assist in maintaining antegrade circulation pressure during intracranial access that may be beneficial to support collateral circulation during a procedure whilst circulation is being compromised by the presence of the various catheters. The pump will also support retrograde flow through the endovascular catheter after a clot has been accessed and the process of removing the clot by aspiration is commenced.

The invention claimed is:

1. A method for navigating a vasculature, comprising the steps of:
    introducing a catheter system through a puncture in a groin, the catheter system comprising:
        a guide catheter;
        a groin-to-brain (G2B) catheter positioned within a lumen of the guide catheter;
        a first diagnostic catheter positioned within a lumen of the G2B catheter;
        a guidewire positioned within a lumen of the diagnostic catheter;
        wherein the G2B catheter is comprised of a sufficient length to reach from the groin to a brain;
    advancing the catheter system to an aortic arch;
    hooking a vessel of the aortic arch with the first diagnostic catheter while the G2B catheter and the guide catheter remain in a descending aorta;
    advancing the guidewire to a cervical artery while the G2B catheter and the guide catheter remain in the descending aorta and the first diagnostic catheter remains hooked to the vessel of the aortic arch;
    advancing the G2B catheter over the guidewire and the first diagnostic catheter to the cervical artery while the guide catheter remains in the descending aorta;
    advancing the guide catheter to the vessel of the aortic arch;
    withdrawing the first diagnostic catheter and the guidewire;
    advancing a second diagnostic catheter through a lumen of the G2B catheter to a target location; and
    advancing the G2B catheter over the second diagnostic catheter to the target location.

2. The method of claim 1, wherein the step of advancing the catheter system to the aortic arch comprises the steps of:
    advancing the guidewire to the aortic arch; and then,
    advancing the first diagnostic catheter to the aortic arch.

3. The method of claim 1, wherein a length of the G2B catheter is greater than a length of the guide catheter.

4. The method of claim 1, wherein a length of the guidewire is greater than a length of the first diagnostic catheter.

5. The method of claim 1, wherein the first diagnostic catheter comprises a pre-shaped curved tip.

6. The method of claim 5, wherein the step of hooking the vessel of the aortic arch with the first diagnostic catheter while the G2B catheter and the guide catheter remain in the descending aorta comprises hooking the vessel of the aortic arch with the pre-shaped curved tip of the first diagnostic catheter.

7. The method of claim 6, wherein a shape of a tip of the second diagnostic catheter is different from the pre-shaped curved tip of the first diagnostic catheter.

8. The method of claim 1, wherein a length of the first diagnostic catheter is greater than a length of the G2B catheter.

9. The method of claim 1, wherein a stiffness of a tip of the first diagnostic catheter is less than a stiffness of a tip of the second diagnostic catheter.

10. The method of claim 1, wherein, after the step of advancing the G2B catheter over the second diagnostic catheter to the target location, a distal portion of the G2B catheter is positioned at or near a cerebral artery, a medial portion of the G2B catheter is positioned at or near a cervical internal carotid artery, and a proximal portion of the G2B catheter is positioned at or near an aortic arch.

11. The method of claim 10, wherein the distal portion of the G2B catheter comprises a length of 20 centimeters, the medial portion of the G2B catheter comprises a length of 15 centimeters, and the proximal portion of the G2B catheter comprises a length of 85 centimeters.

12. The method of claim 11, wherein the G2B catheter is comprised of an aspiration catheter.

13. The method of claim 12, wherein the target location is comprised of a clot.

14. The method of claim 1, further comprising the step of removing the guidewire and introducing a second guidewire.

15. The method of claim 14, wherein the second guidewire has a stiffness greater than a stiffness of the guidewire.

16. The method of claim 1, wherein the G2B catheter comprises a uniform diameter.

17. The method of claim 1, wherein a wall thickness of a proximal portion of the G2B catheter is greater than a wall thickness of a distal portion of the G2B catheter.

18. A method for treating a vascular condition, comprising the steps of:
    introducing a catheter system through a puncture in a groin, the catheter system comprising:
        a guide catheter;
        an aspiration catheter positioned within a lumen of the guide catheter;
        a first diagnostic catheter positioned within a lumen of the aspiration catheter, wherein a distal tip of the first diagnostic catheter comprises a first shape and a first stiffness;
        a guidewire positioned within a lumen of the diagnostic catheter;
    wherein the aspiration catheter is comprised of a sufficient length to reach from the groin to a brain;
    wherein a distal portion of the aspiration catheter comprises a first stiffness, wherein a proximal portion of the aspiration catheter comprises a second stiffness, and wherein the first stiffness is less than the second stiffness;
    wherein a wall thickness of the proximal portion of the aspiration catheter is greater than a wall thickness of the distal portion of the aspiration catheter;
    advancing the catheter system to a descending aorta;
    hooking a left common carotid artery, an innominate artery, or a left subclavian artery with the distal tip of the first diagnostic catheter while the aspiration catheter and the guide catheter remain in the descending aorta;
    advancing the guidewire to a cervical artery while the aspiration catheter and the guide catheter remain in the descending aorta and the first diagnostic catheter remains hooked to the left common carotid artery, the innominate artery, or the left subclavian artery;
    advancing the aspiration catheter over the guidewire and the first diagnostic catheter to the cervical artery while the guide catheter remains in the descending aorta;

advancing the guide catheter to the left common carotid artery, the innominate artery, or the left subclavian artery;

withdrawing the first diagnostic catheter and the guidewire;

advancing a second diagnostic catheter through a lumen of the aspiration catheter to a clot, wherein a distal tip of the second diagnostic catheter comprises a second shape and a second stiffness, wherein the first shape is different from the second shape, and wherein the second stiffness is less than the first stiffness;

advancing the aspiration catheter over the second diagnostic catheter to the clot; and aspirating the clot with the aspiration catheter.

19. A method for navigating a vasculature, comprising the steps of:

introducing a catheter system through a puncture in a groin, the catheter system comprising:

a guide catheter;

a groin-to-brain (G2B) catheter positioned within a lumen of the guide catheter;

a first diagnostic catheter positioned within a lumen of the G2B catheter;

a guidewire positioned within a lumen of the diagnostic catheter;

wherein the G2B catheter is comprised of a sufficient length to reach from the groin to a brain;

advancing the catheter system to an aortic arch;

hooking a vessel of the aortic arch with the first diagnostic catheter while the G2B catheter and the guide catheter remain in a descending aorta;

advancing the guidewire to a cervical artery while the G2B catheter and the guide catheter remain in the descending aorta and the first diagnostic catheter remains hooked to the vessel of the aortic arch;

advancing the G2B catheter over the guidewire;

removing the first diagnostic catheter;

advancing a second diagnostic catheter to the cervical artery while the guide catheter remains in the descending aorta;

advancing the guide catheter to the vessel of the aortic arch;

withdrawing the second diagnostic catheter and the guidewire;

advancing a third catheter through a lumen of the G2B catheter to a target location; and advancing the G2B catheter over the third catheter to the target location.

* * * * *